United States Patent [19]

Abbott et al.

[11] 4,234,684

[45] Nov. 18, 1980

[54] METHOD OF PREPARING MYCOPHENOLIC ACID GLUCOSIDE

[75] Inventors: Bernard J. Abbott, Greenwood; John G. Whitney, Noblesville, both of Ind.

[73] Assignee: Eli Lilly and Company, Indianapolis, Ind.

[21] Appl. No.: 102,504

[22] Filed: Dec. 11, 1979

[51] Int. Cl.³ .......................................... C12P 19/60
[52] U.S. Cl. ................................. 435/75; 435/892; 435/78
[58] Field of Search ............................ 435/75

[56] References Cited

U.S. PATENT DOCUMENTS

| | | | |
|---|---|---|---|
| 3,184,887 | 5/1965 | Winter | 435/75 |
| 3,932,619 | 1/1976 | Brannon et al. | 435/75 |

OTHER PUBLICATIONS

Kieslich, Microbial Transformation of Non-Steroid Cyclic Compounds, pp. 154–158, (1976).

*Primary Examiner*—Alvin E. Tanenholtz
*Attorney, Agent, or Firm*—Nancy J. Harrison; Arthur R. Whale

[57] ABSTRACT

An improved method of preparing mycophenolic acid glucoside which comprises contacting mycophenolic acid with glucose in an aqueous medium in the presence of a glucosylating enzyme selected from that produced by *Streptomyces candidus* NRRL 5449 and that produced by *Streptomyces aureofaciens* NRRL 2209 until mycophenolic acid glucoside is formed.

4 Claims, No Drawings

METHOD OF PREPARING MYCOPHENOLIC ACID GLUCOSIDE

BACKGROUND OF THE INVENTION

1. Field of the Invention

Mycophenolic acid glucoside is useful in the treatment of psoriasis and gout; it also inhibits the growth of transplanted tumor cells in mice and rats (see R. E. Holmes, U.S. Pat. No. 3,903,071).

Mycophenolic acid and mycophenolic acid glucoside have structures 1 and 2, respectively:

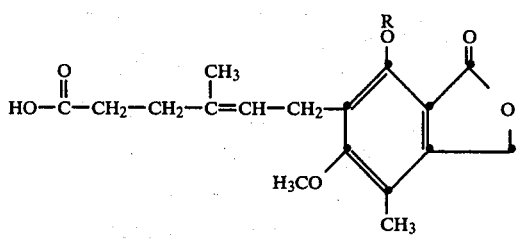

1 R=H (mycophenolic acid);
2 R=β-D-glucopyranosyl (mycophenolic acid glucoside).

A chemical name for mycophenolic acid glucoside is 6-[4-(β-D-glucopyranosyl)-6-methoxy-7-methyl-3-oxo-5-phthalanyl]-4-methyl-4-hexenoic acid.

The method of preparing mycophenolic acid glucoside which is described in U.S. Pat. No. 3,903,071 is a complex chemical one. This method requires many steps and is not very practical on a manufacturing scale.

2. The Prior Art

A group at Imperial Chemical Industries Ltd. (ICI) conducted an extensive screening program for microorganisms that could modify mycophenolic acid. Through their studies, the ICI group found over 20 microbial transformation products of mycophenolic acid. Mycophenolic acid glucoside, however, was not among the products that were found. [See D. F. Jones, et al., *J. Chem. Soc.* (C) 1970, 1725–1737].

There have been examples of microbiological glucosylation of organic compounds. Vanek and his group at the Czechoslovak Academy of Sciences have accomplished glucosylation of dihydroxyanthraquinones. Specific compounds that were glucosylated were alizarin, quinizarin, chrysazin, and anthraflavin. [See Z. Vanek et al., *Folia Microbiol.* 18, 524–526 (1973); N. Hovorkova, et al., *Coll. Czech. Chem. Commun.* 39, 662–667 (1974); and J. Mateju, et al., *Folia Microbiol.* 19, 307–316 (1974)].

Yamada, et al., at the University of Kyoto reported on the glucosylation of pyridoxine. They found that this reaction is catalyzed by various α-glucosidases. The enzymes Takadiastase B (Aspergillus), mold maltase (*A. niger*), and yeast α-glucosidase all catalyzed the glucosylation reaction. [See F. Kawai, et al., *Agr. Biol. Chem.* 35 (2), 184–190 (1971); ibid. 35 (11), 1660–1667 (1971); and ibid. 37 (8), 163–165 (1973)].

More recently, Kieslich, et al., reported that an enzyme produced by *Sporotricum sulfuresens* catalyzed the glucosylation of 5,7-dichloro-2-methyl-8-quinolinol to give the 4-O-methyl-β-glucoside derivative. A 4-O-methyl-β-glucoside derivative of 6-hydroxytetralone was similarly formed. [See K. Kieslich, et al., *Chem. Ber.* 109, 2259–2265 (1976)].

Brannon et al. reported the preparation of a glucosyl derivative of the polyether antibiotic monensin (metabolite A-27106) using the enzyme system of *Streptomyces candidus* NRRL 5449 in U.S. Pat. No. 3,932,619.

Notwithstanding the glucosylation reactions known in the art, it is impossible to predict whether glucosylation will occur when a chemically different substrate is presented. Enzymatic glucosylation of a structure such as that of mycophenolic acid has not been reported. The fact that mycophenolic acid can be successfully glucosylated enzymatically was especially surprising since the extensive microbial transformation studies of the ICI group did not give such a product.

SUMMARY OF THE INVENTION

This invention relates to an improved method of preparing mycophenolic acid glucoside by enzymatic conversion of mycophenolic acid to give mycophenolic acid glucoside. The conversion is effected by contacting mycophenolic acid with glucose in the presence of a glucosylating enzyme selected from that produced by *Streptomyces candidus* NRRL 5449 and that produced by *Streptomyces aureofaciens* NRRL 2209 in an aqueous medium until mycophenolic acid glucoside is produced.

DETAILED DESCRIPTION

This invention relates to a new method for preparing mycophenolic acid glucoside. This method involves enzymatically converting mycophenolic acid to mycophenolic acid glucoside. Enzymatic conversion is accomplished by contacting mycophenolic acid with glucose in the presence of a glucosylating enzyme selected from that produced by *Streptomyces candidus* NRRL 5449 and that produced by *Streptomyces aureofaciens* NRRL 2209 in an aqueous medium until mycophenolic acid glucoside is produced. Mycophenolic acid glucoside can be recovered from the medium by methods known in the art.

Mycophenolic acid is produced by many species of Penicillium, e.g., *P. brevi-compactum, P. stoloniferum, P. scabrum, P. nagemi, P. szaferi, P. patus-mei, P. griscobrunneum,* and *P. viridicatum* [P. W. Clutterbuck et al., *Biochem. J.* 26, 1442–1458 (1932)]. Two strains of *P. stoloniferum* which produce mycophenolic acid, for example, are *P. stoloniferum* NRRL 859 and *P. stoloniferum* NRRL 11078.

In carrying out the method of this invention, either purified mycophenolic acid or partially purified mycophenolic acid may be used as a starting material. The enzyme that glucosylates mycophenolic acid is produced by a strain of *S. aureofaciens* NRRL 2209 or *S. candidus* NRRL 5449.

Cultures bearing an NRRL number are available from the permanent culture collection of the Northern Regional Research Center, United States Department of Agriculture, 1815 North University Street, Peoria, Ill. 61604, under the designated NRRL accession numbers.

Producing the Enzyme

The culture medium used to grow *S. aureofaciens* NRRL 2209 or *S. candidus* NRRL 5449 can be any one of a number of media. For optimal transformation, however, certain culture media are preferred. These media should contain assimilable sources of carbon, nitrogen, and inorganic salts. Preferred sources of carbon are reducing sugars; and a preferred source of nitrogen is soybean meal.

When the conversion is to take place in the fermentation culture at the time *S. aureofaciens* NRRL 2209 or *S. candidus* NRRL 5449 is grown, the medium must contain a source of glucose to achieve efficient conversion. When the microorganism is grown to produce its enzyme for later use in converting mycophenolic acid to mycophenolic acid glucoside, the presence of glucose during fermentation is optional.

Essential trace elements necessary for the growth and development of the organism may occur as impurities in other constituents of the media in amounts sufficient to meet the growth and biosynthetic requirements of the organism. It may be beneficial, however, to incorporate in the culture media additional soluble nutrient inorganic salts capable of yielding iron, sodium, potassium, magnesium, ammonium, calcium, phosphate, chloride, carbonate, sulfate, nitrate and like ions.

The initial pH of the culture medium can be varied. Prior to inoculation with the organism, however, it is desirable to adjust the pH of the culture medium to between about pH 5.7 and about pH 7.5, depending upon the particular medium used. As is the case with other Actinomycetes, the medium gradually becomes more alkaline as the fermentation proceeds and may rise from an initial pH of about pH 5.9 to about pH 6.9 or higher during the growth period of the organism. The final pH is influenced by the initial pH of the medium, the substrate and buffers present in the medium, and the duration of time the organism is permitted to grow. Although pH can be adjusted by addition of either acid or base, good results have been achieved with no adjustment of pH.

In common with other Streptomyces species, the microorganisms require aerobic growth conditions. Small-volume propagation is conveniently carried out on agar slants or plates, in shake flasks or in bottles. For large-scale production, submerged aerobic culture in large tanks is preferred.

The fermentation medium in a sterile tank cna be inoculated with a sporulated suspension to initiate fermentation. Since inoculation with a sporulated suspension involves a growth lag, however, a vegetative inoculum is preferable. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the growth of the vegetative inoculum can be the same as that used for large-scale production, but other media can also be used.

The organism *S. aureofaciens* NRRL 2209 will grow over a temperature range between about 20° C. to about 37° C. Maximum growth and sporulation, however, occur between about 28° C. and about 32° C.

The *S. candidus* NRRL 5449 organism will grow over a temperature range between about 26° C. to about 40° C., with maximum growth and sporulation occuring between about 32° C. and about 37° C.

As is customary in aerobic submerged culture processes, sterile air is blown through the culture medium during fermentation. For efficient growth of the organism and production of mycophenolic acid glucoside, the volume of air used in tank production of the substance should be above about 0.1 volume of air per volume of culture medium per minute (V/V/M). Optimal yields are obtained when the volume of air used is at least one-third to one-half volume of air per volume of culture medium per minute.

The fermentation time needed to effect the conversion varies. The presence of an adequate supply of glucose is essential. In general, when glucose is present in adequate amounts and mycophenolic acid is present in about 0.1 to 1.0 grams per liter of medium, conversion of mycophenolic acid to mycophenolic acid glucoside is essentially complete by about 72 to about 120 hours. Optimal conversion occurs when mycophenolic acid is present in a range of from about 0.2 to about 0.75 grams per liter of medium. An adequate amount of glucose is above one percent of medium by weight. A preferred amount of glucose is from about two to about five percent of medium by weight.

A glucose-sensing test paper may be used to check concentration levels. When glucose content drops below about two percent, glucose should be added to maintain concentration at optimum levels.

Immobilized Enzymes

Yet another method of carrying out the conversion is to immobilize the enzyme by methods known in the art. (See, for example, "Biomedical Applications of Immobilized Enzymes and Proteins", Thomas Ming Swi Chang, Ed., Plenum Press, New York, 1977; Vol. 1.) The immobilized enzyme can then be used in a column (or other suitable type of reactor) to effect the glucosylation reaction.

In addition, the microorganism itself can be immobilized and used to catalyze the glucosylation reaction.

Detection and Assay

Conversion progress can be monitored by thin-layer chromatography (TLC) using UV light for detection. On silica-gel TLC in acetonitrile:water (9:1), the $R_f$ value for mycophenolic acid is about 0.62, whereas the $R_f$ value for mycophenolic acid glucoside is about 0.45.

Isolation

Mycophenolic acid glucoside is present in both the culture broth and in the mycelia. Accordingly, techniques used in the isolation of mycophenolic acid glucoside should be designed to permit maximum recovery of the product from either or both sources. Thus, for example, the fermentation medium is filtered, the pH of the filtrate is lowered to the acidic range, and the acidified filtrate is extracted with a suitable solvent such as chloroform to remove any unreacted mycophenolic acid. In addition, the mycelial cake is extracted with a suitable solvent such as methanol; the organic solvent is removed; and the aqueous solution remaining is added to the filtered broth for the isolation steps. The product is recovered from the solution by methods known in the art. A preferred method of recovery is by adsorption over polymeric resin and elution with a suitable solvent system, such as methanol-water.

EXAMPLE 1

Preparation of Mycophenolic Acid Glucoside Using the *S. aureofaciens* Enzyme

A. Fermentation of *S. aureofaciens*

A lyophilized pellet of *Streptomyces aureofaciens* NRRL 2209 was suspended in water and used to inoculate an agar slant having the following composition:

| Ingredient | Amount |
| --- | --- |
| Dextrin | 10 g |
| Enzymatic Hydrolysate of Casein* | 2 g |
| Beef Extract | 1 g |
| Yeast Extract | 1 g |
| Czapek's Mineral Stock** | 2 ml |
| Agar | 20 g |
| Water | q.s. to 1 liter |
| pH adjusted to 7.3 with 5 N NaOH | |

*N-Z-Amine A, Humko Sheffield Chemical, Lyndhurst, N.J.
**Czapek's Mineral Stock

| | |
| --- | --- |
| KCl | 100 g |
| $MgSO_4 \cdot 7H_2O$ | 100 g |
| Deionized Water | 900 ml |

$FeSO_4 \cdot 7H_2O$ (2 g) was dissolved in 100 ml deionized water containing 2 ml of concentrated HCl. This solution was added to the above $KCl/MgSO_4 \cdot 7H_2O$ solution to complete preparation of the Czapek's Minerals.

Inoculated slants were incubated at 30° C. for 10 days and then stored at 4° C. for no more than 30 days.

A loop inoculum from a slant culture was transferred into 50 ml of vegetative medium in a 250-ml Erlenmeyer flask. The vegetative medium had the following composition:

| Ingredient | Amount |
| --- | --- |
| Glucose | 15 g |
| Soybean Meal | 15 g |
| Corn-Steep Liquor | 10 g |
| Tapioca Dextrin* | 20 g |
| $CaCO_3$ | 4 g |
| Czapek's Mineral Stock | 2 ml |
| Deionized Water | q.s. to 1 liter |
| pH adjusted to 7.0 with 5N NaOH | |

*Stadex 11, A.E. Staley Co., Decatur, Ill.

The inoculated flask was incubated at 30° C. on a rotary shaker operating at 250 rpm. After 48 hours of incubation, 5 ml of culture were transferred to 100 ml of second-stage vegetative medium (having the same composition as the vegetative medium) in a 500-ml Erlenmeyer flask. This culture was incubated for 48 hours at 30° C. on a rotary shaker operated at 250 rpm.

B. Preparation of Mycophenolic Acid Glucoside

Mycophenolic acid (50 mg) was dissolved in water (about 8 ml). The pH was adjusted to 7.0, and water was added to a volume of 10 ml. This solution was added to the flask obtained in Sect. A which contained the *S. aureofaciens* enzyme along with 4 ml of an aqueous solution containing 250 mg/ml of glucose. The flask was then incubated an additional 72 hours.

In order to check the progress of the conversion, aliquots of the fermentation broth were extracted periodically with ethyl acetate. These extracts were examined by silica-gel TLC, using an acetonitrile:water (9:1) solvent system and UV light for detection.

When TLC indicated that substantially all of the mycophenolic acid had been converted to the glucoside, the fermentation was harvested.

Subsequent experiments showed that additional mycophenolic acid and glucose could be added and that incubation could be continued for an additional 24-48 hours to obtain larger quantities of the product.

C. Product Isolation and Purification

A group of 59 flasks containing mycophenolic acid glucoside, obtained as described in Sect. B, were pooled. Broth pH was adjusted from about 7.6 to 4.0 with HCl. Filter aid (Hyflo Super-cel, a diatomaceous earth, Johns-Manville Products Corp.) was added to the pooled broth, and the resulting mixture was separated by filtration. The mycelial mass (containing the filter aid) was extracted with methanol. The methanol extract, recovered by filtration, was concentrated under vacuum to remove the methanol. The resulting aqueous solution was added to the broth filtrate. The pH of this solution was adjusted to 4.0 with HCl. The solution was then extracted with an equal volume of chloroform (in order to remove any remaining mycophenolic acid).

The remaining aqueous solution was concentrated under vacuum to one liter and then chromatographed over a 2.5-ft×40-mm OD column packed with 700 ml of polymeric adsorbent resin (XAD-2, Rohm and Haas Co., Philadelphia, Pa.). The column was washed with 4 L of deionized water and then was eluted with a methanol/water gradient. Column progress was monitored by TLC as described in Sect. B. The stepwise gradient consisted of 4 L of methanol:water (1:7), followed by 8 L methanol:water (1:3), and finally 8 L of methanol:water (1:1). The glucoside was eluted with methanol:water (1:1). Fractions containing mycophenolic acid glucoside were pooled and concentrated in vacuo to give 2.0 g of partially purified product.

Final purification of the mycophenolic acid glucoside was achieved by high-performance liquid chromatography using reversed-phase $C_{18}$ silica-gel (prepared as described in Example 5). Part of the product was obtained from the XAD-2 column (200 mg) was chromatographed over an 11-in×20-mm OD $C_{18}$ silicagel column, packed as described in Example 6. The column was operated at a pressure of 100 psi and a flow rate of 7 ml/min. The column was eluted with water:methanol (65:35), and the column effluent was monitored by UV absorption at 250 nm. Fractions having a volume of 20 ml were collected; mycophenolic acid glucoside was present in fractions 22-33. Fractions containing the glucoside were combined and concentrated in vacuo to give 111 mg of purified mycophenolic acid glucoside. Physical/chemical analyses of this product showed it to be identical to the chemically prepared 6-[4-($\beta$-D-glucopyranosyl)-6-methoxy-7-methyl-3-oxo-5-phthalanyl]-4-methyl-4-hexenoic acid described in U.S. Pat. No. 3,903,071.

EXAMPLE 2

Mycophenolic acid glucoside prepared using the method described in Example 1 except that *S. aureofaciens* is grown in a defined fermentation medium by alternate step A as follows:

A. Fermentation of *S. aureofaciens*

*S. aureofaciens* NRRL 2209 is grown on an agar slant prepared from Bennett's medium. The growth is removed and made up as a slurry with sterile deionized water (10 ml).

This slurry is divided among four 500-ml shake flasks, each containing 100 ml of defined vegetative medium of the following composition:

| Ingredient | Amount |
| --- | --- |
| $(NH_4)_2HPO_4$ | 10.0 |
| $K_2HPO_4$ | 5.0 |
| $Na_2SO_4$ | 0.5 |

-continued

| Ingredient | Amount |
| --- | --- |
| MgSO$_4$ . 7H$_2$O | 0.4 |
| FeSO$_4$ . 7H$_2$O | 0.02 |
| MnSO$_4$ . 1H$_2$O | 0.015 |
| NaCl | 0.02 |
| H$_3$BO$_3$ | 0.0005 |
| CuSO$_4$ . 5H$_2$O | 0.0004 |
| Na$_2$MoO$_4$ . 2H$_2$O | 0.0002 |
| ZnSO$_4$ . 7H$_2$O | 0.008 |
| CaCl | 0.05 |
| CoCl$_2$ . 6H$_2$O | 0.0002 |
| Yeast Extract | 1.0 |
| Glucose* | 10.0 |
| Deionized Water | q.s. to 1.0 liter |

*Glucose sterilized separately and added just prior to inoculation with S. aureofaciens The four inoculated flasks are incubated at 30° C. on a rotary shaker at 250 rpm for 48 hours. This vegetative medium (5-ml portions) is used to inoculate shake flasks (500 ml) containing 100 ml of defined fermentation medium having the same composition as the defined vegetative medium. The inoculated medium is incubated for 48 hours.

EXAMPLE 3

Mycophenolic acid glucoside is prepared by the method described in Example 1 except that the enzyme is that produced by *Streptomyces candidus* NRRL 5449 by alternate step A as follows:

A. Fermentation of S. candidus

*S. candidus* NRRL 5449 is grown on an agar slant prepared from Bennett's medium to give a well-defined colony. The colony is removed and made up as a slurry with sterile deionized water (10 ml).

This slurry is divided among four 500-ml shake flasks, each containing 100 ml of vegetative medium of the following composition:

| Ingredient | Amount |
| --- | --- |
| Corn Distillers' Solubles* | 25.0 g |
| Lactose | 10.0 g |
| Maltose | 10.0 g |
| FeSO$_4$ . 7H$_2$O | 0.01 g |
| MgSO$_4$ . 7H$_2$O | 2.0 g |
| KH$_2$PO$_4$ | 2.0 g |
| CaCO$_3$ | 2.0 g |
| Deionized water | q.s. to 1.1 liter |

*Nadrisol, National Distiller's Products Company

The four inoculated flasks are incubated at 30° C. on a rotary shaker at 250 rpm for 24 hours. This vegetative medium (10-ml portions) is used to inoculate shake flasks (500 ml) containing 100 ml of sterilized fermentation medium of the following composition:

| Ingredient | Amount |
| --- | --- |
| Beef extract | 5 g |
| Casein pancreatic hydrolysate peptone | 5 g |
| NaCl | 5 g |
| Glycerol | 15 g |
| CaCO$_3$ | 2 g |
| Deionized water | q.s. to 1 liter |
| pH 7.2, not adjusted | |

The inoculated medium is incubated for 72 hours as described above.

EXAMPLE 4

Production of Mycophenolic Acid Glucoside by a Particulate *S. candidus* Enzyme

*S. candidus* NRRL 5449 is grown as described in Example 3. The cells are separated from the fermentation medium by vacuum filtration and are divided into 200-g aliquots which are stored by freezing. Two of these aliquots are thawed at room temperature and are suspended in 0.05 M phosphate buffer (pH 5.8) to a final volume of 600 ml. This cell suspension is sonicated for 30 minutes, and the sonicate is centrifuged at 10,000 rpm for 30 minutes. The resulting cell debris is suspended in 100 ml of the phosphate buffer; this suspension is dialyzed for 18 hours with 5 L of the chilled, phosphate buffer. To 50 ml of the particulate dialyzed enzyme are added D-glucose and mycophenolic acid dissolved in ethanol. The reaction mixture is stirred for 72 hours at 30° C. and then is filtered; the filtrate is extracted with chloroform. This chloroform extract is concentrated under vacuum and then is purified by chromatography to give mycophenolic acid glucoside.

EXAMPLE 5

Preparation of Silica Gel/C$_{18}$ Reversed Phase Resin

Step 1: Hydrolysis

LP-1 silica gel (1000 g from Quantum Corp., now Whatman) is added to a mixture of concentrated sulfuric acid (1650 ml) and concentrated nitric acid (1650 ml) in a 5-L round-bottom flask and shaken for proper suspension. The mixture is heated on a steam bath overnight (16 hours) with a water-jacketed condenser attached to the flask.

The mixture is cooled in an ice bath and carefully filtered using a sintered-glass funnel. The silica gel is washed with deionized water until the pH is neutral. The silica gel is then washed with acetone (4 L) and dried under vacuum at 100° C. for 2 days.

Step 2: First Silylation

The dry silica gel from Step 1 is transferred to a round-bottom flask and suspended in toluene (3.5 L). The flask is heated on a steam bath for 2 hours to azeotrope off some residual water. Octadecyltrichlorosilane (321 ml, Aldrich Chemical Company) is added, and the reaction mixture is refluxed overnight (16 hours) with slow mechanical stirring at about 60° C. Care is taken so that the stirrer does not reach near the bottom of the flask. This is to prevent grinding the silica gel particles.

The mixture is allowed to cool. The silanized silica gel is collected, washed with toluene (3 L) and acetone (3 L), and then air-dried overnight (16–20 hours). The dried silica gel is suspended in 3.5 L of acetonitrile:water (1:1) in a 5-L flask, stirred carefully at room temperature for 2 hours, filtered, washed with acetone (3 L) and air-dried overnight.

Step 3: Second Silylation

The procedure from the first silylation is repeated using 200 ml of octadecyltrichlorosilane. The suspension is refluxed at 60° C. for 2 hours while stirring carefully. The final product is recovered by filtration, washed with toluene (3 L) and methanol (6 L), and then dried under vacuum at 50° C. overnight (16–20 hours).

EXAMPLE 6

Slurry Packing Procedure for Michel-Miller Columns
General Information

A. Analytical or preparative columns can be packed by this procedure.

B. Silica gels and silica gel reversed phase packings (e.g., Quantum LP-1, particle size 10–20 microns; Li-Chroprep RP-8 and RP-18, particle size 25–40 microns) are recommended. However, other silica gels (e.g., Shandons ODS Hypersil, particle size 5 microns) as well as other types of resins have been packed successfully by this procedure.

C. Generally, a pressure of less than 200 psi and flow rates between 5–40 ml/minute are required for this slurry packing technique; this is dependent on column volume and size. PLEASE NOTE: Packing pressure should exceed pressure used during actual separation by 30–50 psi; this will assure no further compression of the adsorbent during separation runs. Columns packed by this procedure with reversed-phase silica gel can be operated for several years without loss of efficiency.

D. Sudden decrease in pressure may cause cracks or channels to form in the packing material, which would greatly reduce column efficiency. Therefore, it is important to let the pressure drop slowly to zero whenever the pump has been turned off.

E. Approximate volume of columns (Ace Glass Cat. No., unpacked): 5795-04, 12 ml; 5795-10, 110 ml; 5795-16, 300 ml; 5795-24, 635 ml; and 5796-34, 34 ml.

F. The time required to pack a glass column will vary from minutes to several hours depending on column size and experience of the scientist.

Example

1. Connect glass column to a reservoir column via coupling (volume of reservoir column should be twice that of the column). Place both columns in vertical positions (reservoir column above).

2. Weigh out packing material (ca. 100 g for 200 ml column).

3. Add ca. five volumes of solvent to packing material; use a mixture of 70–80% methanol and 20–30% water.

4. Shake well until all particles are wetted, let stand overnight or longer to assure complete soaking of particles by solvent. Decant supernatant.

5. Slurry the resin with sufficient solvent to fill reservoir column. Pour swiftly into reservoir. NOTE: The column must be pre-filled with the same solvent and the reservoir column should be partly filled with solvent before slurry is poured. The use of larger slurry volumes may also provide good results; however, this will require (a) larger reservoir or (b) multiple reservoir fillings during the packing procedure.

6. Close reservoir with the Teflon plug beneath the column (see FIG. 1 of U.S. Pat. No. 4,131,547, plug No. 3); connect to pump; and immediately start pumping solvent through system at maximum flow rate if Ace Cat. No. 13265-25 Pump or similar solvent-delivery system is used (ca. 20 ml/minute).

7. continue until column is completely filled with adsorbent. Pressure should not exceed maximum tolerance of column during this operation (ca. 200 psi for large columns and 300 psi for analytical columns). In most cases, pressures less than 200 psi will be sufficient.

8. Should pressure exceed maximum values, reduce flow-rate; pressure will drop.

9. After column has been filled with adsorbent, turn off pump; let pressure drop to zero; disconnect reservoir; replace reservoir with a pre-column; fill pre-column with solvent and small amount of adsorbent; and pump at maximum pressure until column is completely packed. For additional information, see general procedure.

NOTE: Always allow pressure to decrease slowly after turning off pump—this will prevent formation of any cracks or channels in the packing material.

10. Relieve pressure and disconnect pre-column carefully. With small spatula remove a few mm (2–4) of packing from top of column; place 1 or 2 filter(s) in top of column; gently depress on top of packing material, and place Teflon plug on top of column until seal is confirmed. Connect column to pump, put pressure on (usually less than 200 psi) and observe through glass wall on top of column if resin is packing any further. If packing material should continue to settle (this may be the case with larger columns), some dead space or channelling will appear and step 9 should be repeated.

We claim:

1. The method of producing mycophenolic acid glucoside which comprises contacting mycophenolic acid with glucose in the presence of a glucosylating enzyme selected from that produced by *Streptomyces candidus* NRRL 5449 and that produced by *Streptomyces aureofaciens* NRRL 2209 in an aqueous medium until a substantial amount of mycophenolic acid glucoside is produced.

2. The method of claim 1 wherein the enzyme is produced by *Streptomyces aureofaciens* NRRL 2209.

3. The method of claim 1 wherein the enzyme is produced by *Streptomyces candidus* NRRL 5449.

4. The method of claims 1, 2 or 3 wherein the enzyme is present in the culture medium in which it is produced.

* * * * *